(12) United States Patent
Abreu et al.

(10) Patent No.: US 7,271,594 B2
(45) Date of Patent: Sep. 18, 2007

(54) SYSTEM AND METHOD FOR POWER RATIO DETERMINATION WITH COMMON MODE SUPPRESSION THROUGH ELECTRIC FIELD DIFFERENCING

(75) Inventors: Rene Abreu, New Fairfield, CT (US); Jeffrey Grotts, Danbury, CT (US); Alexander J. Majewski, Fairfield, CT (US)

(73) Assignee: Goodrich Corporation, Charlotte, NC (US)

( * ) Notice: Subject to any disclaimer, the term of this patent is extended or adjusted under 35 U.S.C. 154(b) by 302 days.

(21) Appl. No.: 11/095,180

(22) Filed: Mar. 31, 2005

(65) Prior Publication Data

US 2006/0226348 A1 Oct. 12, 2006

(51) Int. Cl.
*G01R 29/12* (2006.01)
(52) U.S. Cl. ..................................... 324/457
(58) Field of Classification Search .............. 324/457
See application file for complete search history.

(56) References Cited

U.S. PATENT DOCUMENTS

| | | | | |
|---|---|---|---|---|
| 5,883,518 A | * | 3/1999 | Borden | 324/750 |
| 5,966,019 A | * | 10/1999 | Borden | 324/750 |
| 6,348,683 B1 | | 2/2002 | Verghese et al. | |
| 6,500,618 B1 | | 12/2002 | Woolard et al. | |
| 2002/0067480 A1 | | 6/2002 | Takahashi | |
| 2004/0114939 A1 | * | 6/2004 | Taylor | 398/152 |

FOREIGN PATENT DOCUMENTS

WO    WO 2004/083796 A1    9/2004

* cited by examiner

*Primary Examiner*—Walter Benson
*Assistant Examiner*—Timothy J Dole
(74) *Attorney, Agent, or Firm*—Alston & Bird LLP

(57) ABSTRACT

A system for processing signals includes a receiver assembly for receiving a signal. The signal has a sample component with a sample electric field and a sample polarization, and has a reference component with a reference electric field and a reference polarization. The receiver assembly includes an analyzer for polarimetrically processing the signal, including differencing the signal to generate a difference electric field proportional to the difference of the sample and reference electric fields. By polarimetrically differencing the signal, the analyzer reduces the magnitude of the common-mode signal at the difference signal receiver. The receiver assembly includes an electric-field detector for measuring the difference electric field such that the reduction in common-mode amplitude decreases the noise equivalent power of the electric-field detector. One advantage of the present invention, then, is the reduction of noise equivalent power of the electric-field detector when measuring small variations in large electric fields.

8 Claims, 5 Drawing Sheets

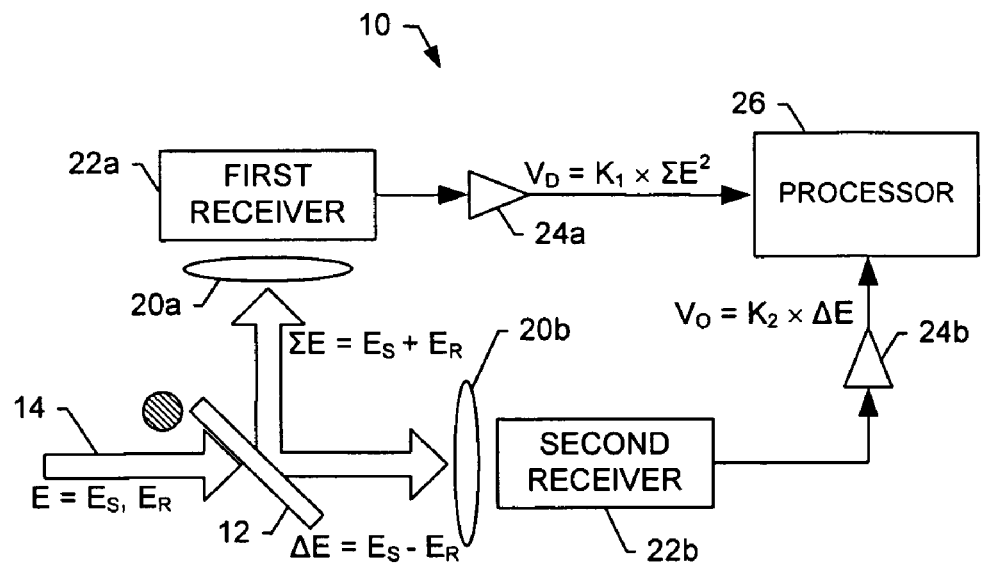
FIG. 1.
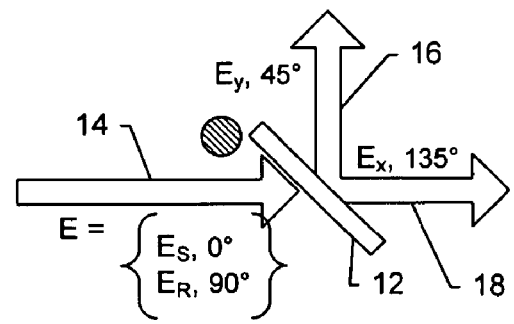

SYSTEM AND METHOD FOR POWER RATIO DETERMINATION WITH COMMON MODE SUPPRESSION THROUGH ELECTRIC FIELD DIFFERENCING

FIELD OF THE INVENTION

The present invention generally relates to detecting the power of electromagnetic signals and, more particularly, to detecting the ratio of power of electromagnetic signals propagated through two media of different transmissions. Detection of trace amounts of absorbed power is enhanced by the method of this invention enabling the field of spectroscopy with greatly improved sensitivity. The invention enhances the sensitivity of heterodyne detection of electric field differences by reducing the magnitude of large common mode field amplitudes for any differential-measurement application, particularly in the Terahertz region of the electromagnetic spectrum.

BACKGROUND OF THE INVENTION

In many contexts it is desirable to detect electromagnetic radiation signals, such as in spectroscopy, refractive index measurements or the like. Conventionally, such radiation may be detected by means of a power detector whose output voltage is proportional to input power (watts). Such power detectors include, for example, thermistor bolometers, thermopile detectors, silicon diode photon detectors and the like. In an alternative technique, an electric-field sensing system detects electromagnetic radiation by producing an output voltage proportional to the electric-field strength (volts/meter) in the region around an input antenna. Examples of these systems include, for example, conventional radio receivers, television receivers, radar receivers and the like. Electric-field sensing systems lend themselves to heterodyne detection and typically exhibit a significantly lower noise-equivalent power than power detectors, and are therefore better adapted to receive lower-power beams. Nonetheless, in various contexts, the maximum sensitivities permitted by such conventional electric-field sensing systems are being challenged, and even exceeded.

More particularly in the context of spectroscopy, for example, data for chemical and biological agents such as the Anthrax stimulant *Bacillus Subtilis* (BG) indicates the need for spectral measurements over a wide frequency range with challenging sensitivity. Typically, measurements are taken from dense samples of BG spores prepared at concentrations high enough to be measured by a conventional Fourier Transform spectroscopy (FTS) instrument. At these concentrations, resonances may be damped by the density of spores in the sample. As will be appreciated, measurements on samples in low density aerosol form may provide better characterization of biological warfare agents (BWAs) in representative scenarios. However, measurements on such samples require spectrometer sensitivities not available in today's laboratory spectrometers. As such, it would be desirable to design a system and method for detecting very low power electromagnetic signals absorbed by low concentration samples with better sensitivity than that of currently available systems and methods.

SUMMARY OF THE INVENTION

In light of the foregoing background, embodiments of the present invention provide an improved system and method of detecting the power of electromagnetic signals, as such may be applied in the context of spectroscopy. In accordance with embodiments of the present invention, the power of electromagnetic signals can be detected with improved noise performance, and thus increased sensitivity, by suppressing or otherwise rejecting the large common mode signal that degrades performance in heterodyned detection systems. The electric field of the signals can then be detected in lieu of the power, the power being calculable from the electric field.

According to one aspect of the present invention, a system is provided that includes a receiver assembly for receiving a signal. The signal has a sample component with a sample electric field and a sample polarization, and has a reference component with a reference electric field and a reference polarization, where the reference polarization is offset from the sample polarization. The receiver assembly includes an analyzer for polarimetrically processing the signal to generate an electric field proportional to the difference of the sample and reference electric fields. By polarimetrically differencing the signal, the analyzer reduces the magnitude of the common-mode amplitude at the receiving detector. The receiver assembly also includes an electric-field detector (e.g., heterodyne receiver) for measuring the difference electric field such that the reduction in common-mode amplitude increases the sensitivity of the electric-field detector.

The analyzer is further capable of summing the signal to generate a sum electric field proportional to the sum of the sample and reference electric fields. Accordingly, the receiver assembly may further include a power detector for measuring a sum power based upon the sum electric field. A processor can then calculate a power ratio based upon the measured difference electric field and the measured sum power.

As will be appreciated, the signal may be received in any of a number of different manners. In the context of spectroscopy, for example, the system further includes a beamsplitter for generating first and second beams from a source beam, such as a source beam having a frequency in the THz region of the electromagnetic spectrum. A sample cell, which includes a sample medium and a base medium, receives the first beam and outputs a sample signal with a sample electric field. Similarly, a reference cell, which includes the base medium, receives the second beam and outputs a reference signal with a reference electric field.

In such instances, the processor can further be capable of computing the absorption spectrum of the sample medium based upon the power ratio of the measured difference electric field and the measured sum power. This power ratio is representative of the absorption spectrum of the sample medium. More particularly, the system can include a transmitter for scanning the source beam through a plurality of transmission frequencies. For each transmission frequency, the beamsplitter, sample cell, reference cell, polarizing beamsplitter, analyzer, electric-field detector, power detector, and processor are capable of generating first and second beams, outputting a sample signal, outputting a reference signal, combining the sample and reference signals, measuring the difference electric field, measuring the sum power, and calculating a power ratio for each transmission frequency. The power ratio at each transmission frequency is representative of the transmission of the sample. Accordingly, the processor can be capable of defining a measured absorption signature for the sample medium based upon the transmissions and associated frequencies, and thereafter identifying the sample medium based upon the measured absorption signature.

Embodiments of the present invention therefore provide an improved system and method for processing a signal through electric-field differencing. In accordance with embodiments of the present invention, a receiver assembly includes a highly-sensitive electric-field detector. Detection and amplification is applied to the difference between sample and reference electric fields. In this regard, by differencing the sample and reference electric fields, the system of embodiments of the present invention removes the large common mode (average) electric field component, thereby increasing the gain of the receiver and accordingly providing superior noise performance, particularly when voltage noise of a post receiver amplifier operates as the dominant source of noise. As such, the system and method of embodiments of the present invention improve the noise performance of prior electric field sensing techniques.

BRIEF DESCRIPTION OF THE DRAWINGS

Figure 2:
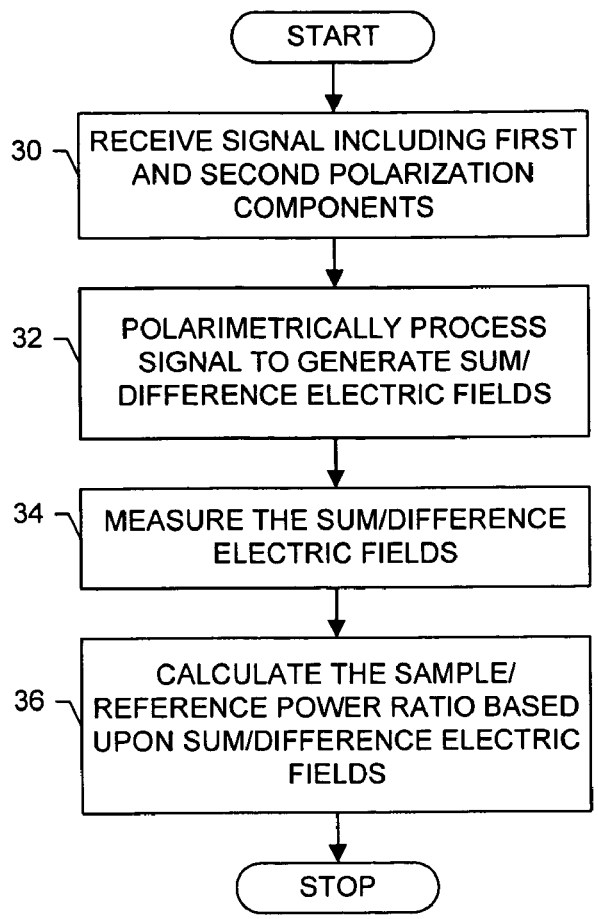
Figure 3:
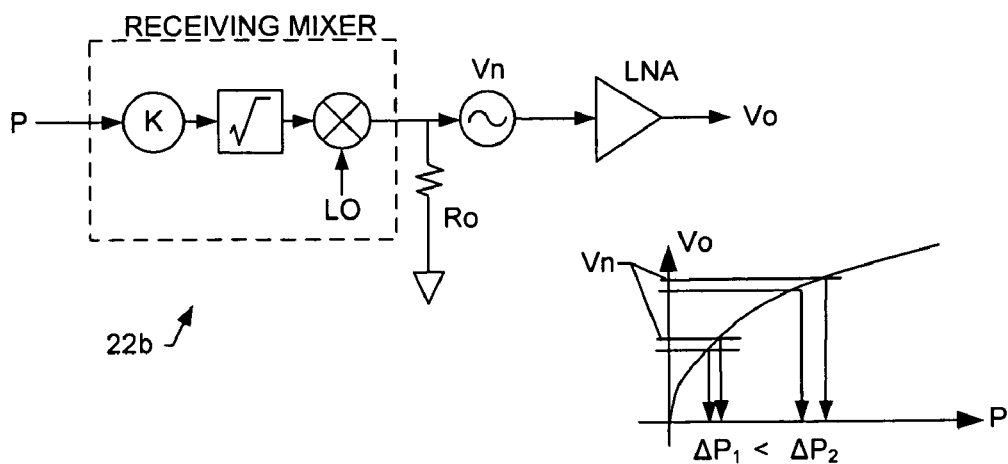
Figure 4:
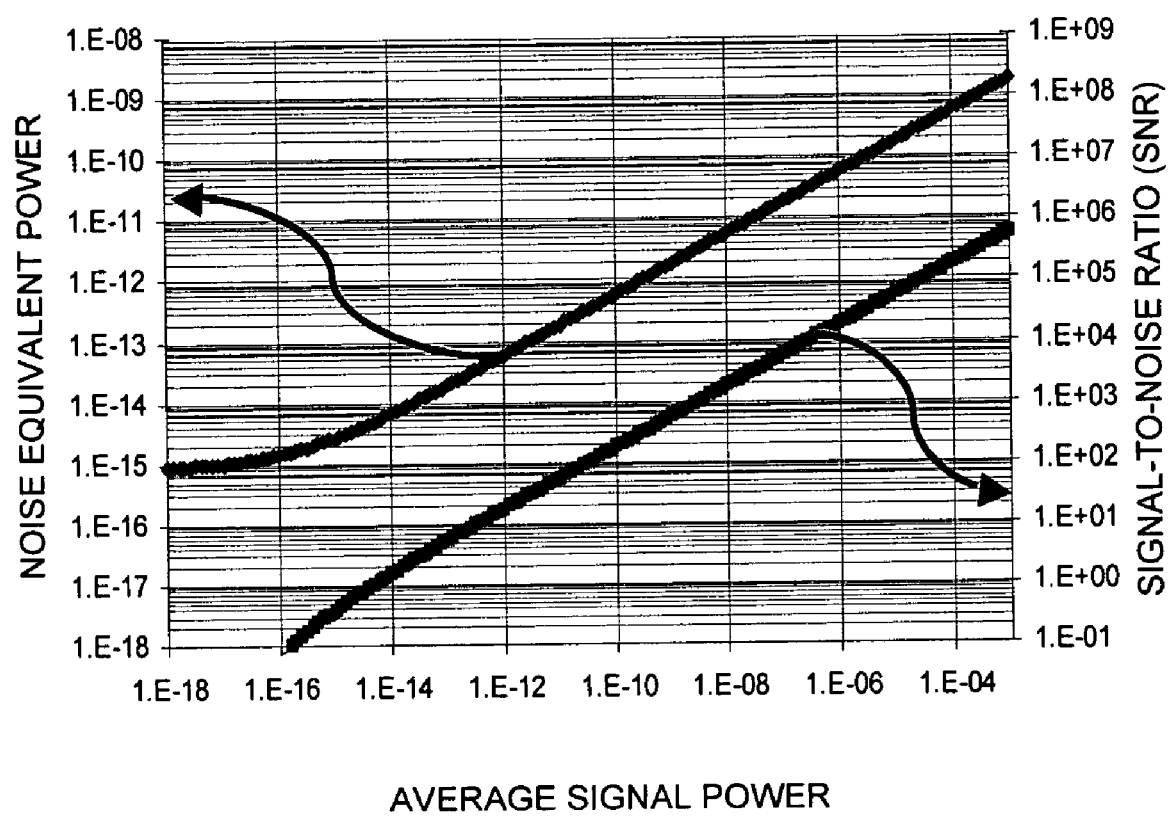
Figure 5:
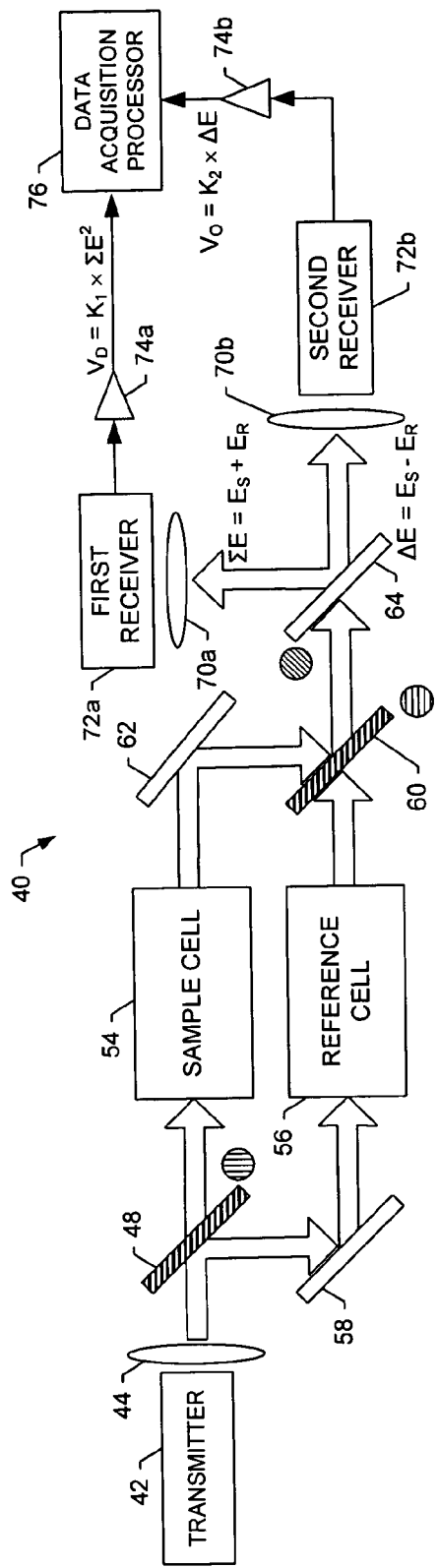
Figure 6:
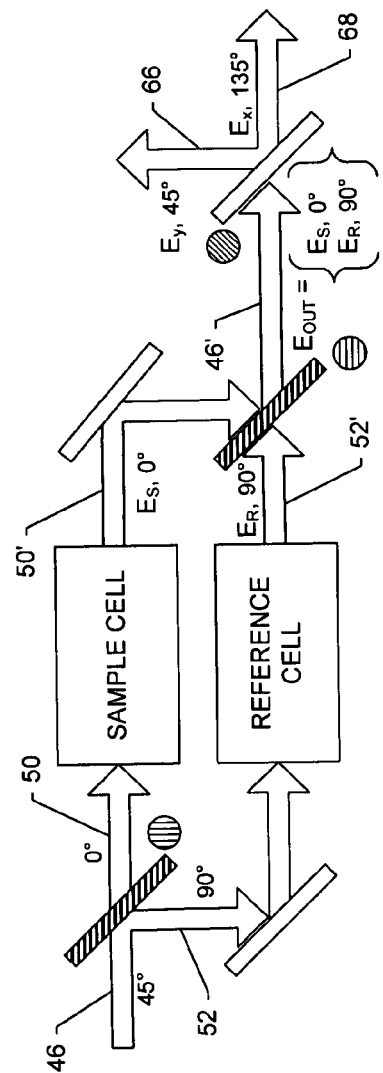
Figure 7:
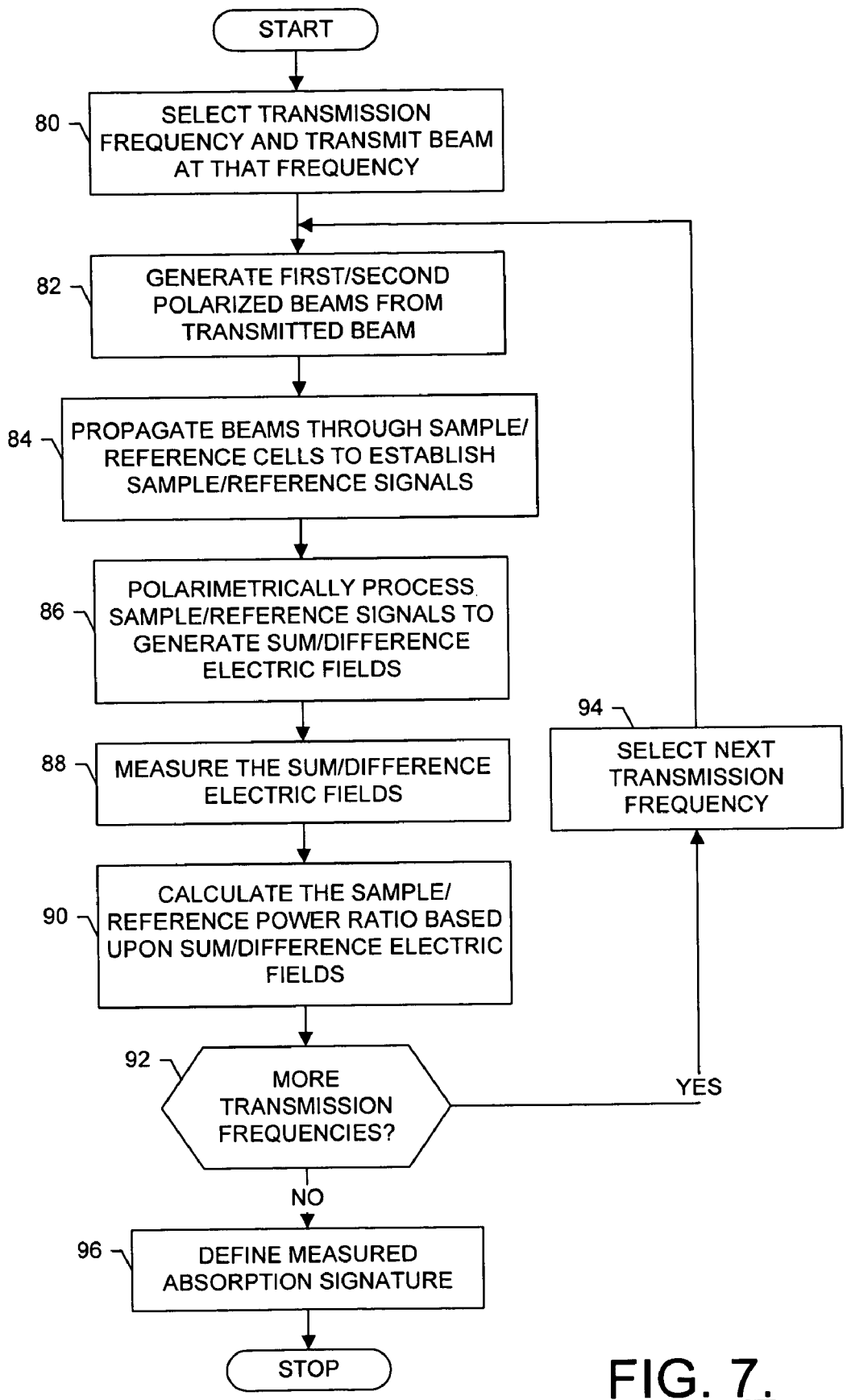

Having thus described the invention in general terms, reference will now be made to the accompanying drawings, which are not necessarily drawn to scale, and wherein:

FIG. 1 is a schematic block diagram of a receiver assembly, in accordance with one embodiment of the present invention;

FIG. 2 is a flowchart illustrating various steps in a method of receiving and processing a signal beam of light, in accordance with one embodiment of the present invention;

FIG. 3 is a schematic block diagram of a photomixer receiver assembly, in accordance with one embodiment of the present invention;

FIG. 4 is a graph illustrating the noise equivalent power and signal-to-noise ratio (SNR) as a function of average input power for a photomixer receiver, in accordance with one embodiment of the present invention;

FIG. 5 is a schematic block diagram of a spectrometer system in accordance with one embodiment of the present invention;

FIG. 6 is a schematic block diagram of the spectrometer system of FIG. 5 illustrating polarization of the signals propagating through various stages of the system; and FIG. 7 is a flowchart illustrating various steps in a method of identifying a sample in accordance with one embodiment of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring to FIGS. 1 and 2, a receiver assembly 10 and method for receiving and processing a signal beam of light are shown in accordance with one embodiment of the present invention. As shown, the assembly includes an analyzer 12 for receiving a signal comprising a beam of light 14 having a first, or sample, component with a sample electric field $E_S$ and a first polarization, as shown in block 30. In addition, the beam has a second, or reference, component with a reference electric field $E_R$ and a second polarization, where the second polarization is offset from the first polarization. In one embodiment for example, the sample and reference components have polarizations that are orthogonally offset, with the sample component having a 0° polarization, and the reference component having a 90° polarization, as shown in the inset of FIG. 1.

The analyzer 12 is rotated at half the polarization offset between the electric-field components of the signal 14. Thus, for a signal including sample and reference electric-field components at 0° polarization and 90° polarization, respectively, the analyzer is rotated at 45° to the sample and reference electric-field component polarization planes. The analyzer is capable of at least partially polarimetrically processing the signal to generate sum and difference electric fields, as shown in block 32 of FIG. 2. More particularly, the analyzer divides the signal into two parts, a sum signal 16 and a difference signal 18. Continuing the above example, then, the analyzer can divide the signal into a sum signal of light having a 45° polarization, and a difference signal of light having a 135° polarization. Although the analyzer 12 divides the signal into sum and difference signals 16, 18, the sum signal has an electric field $E_y$ proportional to the sum of the electric fields of the sample and reference electric-field components (i.e., $E_y=(1/\sqrt{2})(E_S+E_R)$). In contrast, the difference signal has an electric field $E_x$ proportional to the difference of the electric fields of the sample and reference electric-field components (i.e., $E_x=(1/\sqrt{2})(E_S-E_R)$).

Following the analyzer 12, the sum signal 16 propagates to a first focusing lens 20a, from which the focused sum signal is picked up or otherwise received by a first receiver 22a. Similarly, the difference signal 18 propagates to a second focusing lens 20b, from which the focused difference signal is picked up or otherwise received by a second receiver 22b. The first and second receivers obtain measurements representative of the electric field sum $E_y$ and electric field difference $E_x$ of the sum and difference signals, respectively, as shown in block 34 of FIG. 2. As will be appreciated, the first receiver can comprise any of a number of different types of receivers including, for example, a power detector such as a bolometer, an electric-field detector such as a photomixer receiver (heterodyne receiver), or the like. As will be appreciated by those skilled in the art, when the signal power is significantly higher than the noise floor of a power detector, a power detector is sufficiently adapted to receive such signals. Thus, in one advantageous embodiment, the first receiver comprises a power detector. In such instances, when the first receiver comprises a bolometer, the bolometer includes a transducer element with has an electrical resistance that varies as a result of radiation changes produced by the sum signal power. By detecting changes in the electrical resistance, the bolometer obtains a measure of the radiation power, or the square of the electric field sum $E_y$.

The second receiver 22b, on the other hand, comprises an electric-field detector such as a photomixer receiver (heterodyne receiver), an example of which is shown more particularly in FIG. 3. As will also be appreciated by those skilled in the art, electric-field detectors such as heterodyned photomixer receivers typically exhibit a significantly lower noise-equivalent power than room temperature power detectors, and are therefore better adapted to receive lower-power beams. In this regard, since forming the electric field difference $E_x$ effectively removes the large common mode (average) electric field component at the input to the receiver, the largest theoretical gain can be achieved for the second receiver, thereby providing superior noise performance, particularly when voltage noise of a post receiver amplifier operates as the dominant source of noise.

As shown in FIG. 3, a second receiver 22b comprising an electric-field detector, and more particularly a photomixer receiver, may include a high-speed photoconductor. In the photomixer receiver, the difference signal 18 at the received frequency (e.g., $\omega$) is combined with a local oscillator beam of light at a frequency $\omega_{LO}$, and thereafter focused on the photomixer. The photomixer receiver, in turn, generates a current or voltage signal at an intermediate difference frequency (e.g., $\omega - \omega_{LO}$), where the generated signal varies as a result of radiation changes produced by the difference beam. By detecting changes in the generated signal, the photomixer receiver obtains a measure of the radiation, or electric field difference $E_x$. For more information on such a photomixer receiver, see U.S. Pat. No. 6,348,683 entitled: *Quasi-Optical Transceiver Having an Antenna with Time Varying Voltage,* issued Feb. 19, 2002.

To further illustrate the advantage of embodiments of the present invention, consider that the noise equivalent power can be evaluated based upon the photomixer receiver conversion loss, which can be represented as follows:

$$P_i \times \eta_{cl} = \frac{V_o^2}{R_o} \tag{1}$$

where $P_i$ represents the input power, $\eta_{cl}$ represents the mixer conversion loss, and $V_o^2/R_o$ represents the mixer intermediate frequency (IF) power. Also, consider that the mixer IF voltage $V_o$ can be represented in terms of the noise voltage $V_n$ and variable K, which is related to the photomixer antenna power coupling efficiency and can be represented as $K = R_o \times \eta_{cl}$. More particularly, the mixer IF voltage can be represented as follows:

$$V_o = V_n + \sqrt{K \times P_i} \tag{2}$$

Based upon the expressions of equations (1) and (2), consider that the total noise equivalent input power can be calculated in terms of the total equivalent signal power, $P_{sig}$, and the total equivalent noise power, $P_{noise}$, as follows:

$$(P_{sig} + P_{noise}) \times \eta_{cl} = \frac{V_o^2}{R_o} = \frac{1}{R_o} \times \left[ V_n + \sqrt{K \times P_{sig}} \right]^2 \tag{3}$$

Rearranging the terms of equation (3), then, the total equivalent noise power can be expressed in the following manner:

$$P_{noise} = \frac{V_n^2}{R_o} \times \frac{1}{\eta_{cl}} + 2 \times \frac{V_n^2}{R_o} \times \frac{1}{\eta_{cl}} \times \sqrt{\eta_{cl} \times \frac{P_{sig}}{(V_n^2/R_o)}} \tag{4}$$

As can be seen from the expression of equation (4), the total equivalent noise power is the reflected electronic noise power with an added excess noise term proportional to the square root of the ratio of the input signal power to the electric noise power. As shown in FIG. 4, the noise equivalent power, as well as the signal-to-noise ratio (SNR) is proportional to the input signal power, or average signal power. Thus, reducing the average signal power received by the second receiver 22b via electric field differencing (i.e., $E_x$) the receiver assembly likewise reduces the noise equivalent power of the second receiver.

Referring back to FIG. 1, following the first receiver 22a, the measured sum power $(\Sigma E)^2$ can, but need not, be passed to a first amplifier 24a having a first scaling constant $K_1$. Similarly, the measured electric field difference $(\Delta E)$ can, but need not, be passed from the second receiver 22b to a second amplifier 24b having a second scaling constant $K_2$. Thereafter, the amplified, measured electric field sum and difference are received by a processor 26, which is capable of storing and/or processing the electric field sum and difference for one or more of a number of different purposes. In this regard, the processor can comprise any of a number of different processing devices capable of operating in accordance with embodiments of the present invention including, for example, a personal computer, laptop computer, server computer, workstation computer, or the like.

Generally, by measuring the sum power (i.e., $E_y^2 = (E_S + E_R)^2$) and the electric field difference (i.e., $E_x = E_S - E_R$), the processor 26 can calculate the power ratio associated with the sample and reference components $E_S$, $E_R$ of the signal 14 based upon the measured sum power and electric field difference, as shown in block 36 of FIG. 2. In this regard, the ratio of the power of the sample component $P_S$ and the power of the reference component $P_R$ can be expressed notationally as follows:

$$\frac{P_S}{P_R} = \left(\frac{E_S}{E_R}\right)^2 = \left(\frac{E_R + (E_S - E_R)}{E_R}\right)^2 = \left(\frac{\Delta E}{E_R}\right)^2 + 2\frac{\Delta E}{E_R} + 1 \tag{5}$$

where $\Delta E = E_S - E_R$. To further reduce the expression, when the power ratio approaches unity (as is the case with trace amount of absorption in spectroscopy contexts, as explained below), the electric field sum can be approximated as follows:

$$\Sigma E = E_S + E_R \approx 2 E_R \tag{6}$$

Combining equations (5) and (6), the processor can approximate the power ratio in terms of the electric field sum and difference in the following manner:

$$\frac{P_S}{P_R} = 4 \times \left[ \left(\frac{\Delta E}{\Sigma E}\right)^2 + \frac{\Delta E}{\Sigma E} \right] + 1 \tag{7}$$

As can be seen, then, the power ratio of the sample and reference components is readily calculated based upon the electric field sum and electric field difference, which in spectroscopy contexts, provides better trace signal sensitivity than obtained when calculating a small deviation of power ratio based upon approximately equal electric field vectors of the sample and reference components.

To further illustrate the advantages of embodiments of the present invention, reference is now made to FIGS. 5, 6 and 7, which illustrate a spectrometer system and method that would benefit from embodiments of the present invention. It should be understood, however, that the spectrometer system and method illustrated and hereinafter described are merely illustrative of one type of system and method that would benefit from embodiments of the present invention and, therefore, should not be taken to limit the scope of the present invention. In this regard, while several embodiments of the spectrometer system and method are illustrated and will be hereinafter described for purposes of example, other types of systems and methods of detecting the power of electromagnetic signals can readily employ the present invention. Moreover, the system and method of the present invention will be primarily described in conjunction with spectral signature analysis to detect biological materials, particularly in the THz (or mmW) region of the electromagnetic spectrum. But the system and method of embodiments of the present invention can be utilized in conjunction with a variety of other applications, both within and outside the context of detecting biological materials, and within and outside the THz region of the electromagnetic spectrum.

As shown in FIGS. 5 and 6, a spectrometer system 40 of one embodiment of the present invention includes a transmitter 42 for transmitting a beam of coherent light (electromagnetic wave) at a given frequency. The transmitter can comprise any of a number of different transmitters known to those skilled in the art. In one advantageous embodiment, for example, the transmitter comprises an optical heterodyne (photo) mixer transmitter (i.e., photomixer transmitter). In such instances, the transmitter includes a high-speed photoconductive diode (i.e., photomixer), which is pumped with two laser sources having offsetting frequencies at $\omega_1$ and $\omega_2$. The inherently quadratic nature of the cross-gap absorption then creates a difference (i.e., transmission) frequency (i.e., $\omega_1-\omega_2$) in the photocurrent induced in the diode. By locating the photomixer at the driving point of an antenna, such as a spiral, dipole or slot antenna, the difference-frequency current is converted to difference-frequency photons. The result is a highly-tunable, continuous-wave (cw), highly-coherent source of light contained in a single (quasi-Gaussian) spatial mode. For more information on such a transmitter, see the aforementioned '683 patent.

Thus, the method of one embodiment includes selecting a transmission frequency, thereafter transmitting a beam of light (i.e., source beam) at that frequency from the transmitter 42, as shown in block 80 of FIG. 7. The transmission frequency can be selected in any of a number of different manners. To detect a sample based upon a measured absorption signature, as explained below, however, the transmission frequency is typically selected within a range of frequencies over which the absorption signature is defined. In a photomixer transmitter, then, the photomixer can be pumped with a laser source at a fixed frequency $\omega_2$, and a laser source at a tunable frequency $\omega_1$ that is selected to thereby select the difference, or transmission, frequency (i.e., $\omega_1-\omega_2$).

The beam of light from the transmitter 42 passes through a collimating lens 44 to produce a collimated beam of light 46 having a 45° polarization. The polarized beam then passes to a first polarizing beamsplitter 48. The first polarizing beamsplitter, in turn, divides the beam of light into two parts, a first beam of light 50 and a second beam of light 52, having a 90° polarization offset, as shown in block 82 of FIG. 7. For example, the first polarizing beamsplitter can divide the beam of light into a first beam of light having a 0° polarization, and a second beam of light having a 90° polarization. As shown in block 84, the first beam of light passes from the first polarizing beamsplitter through a sample cell 54 that includes a sample medium (e.g., chemical or biological agent) to be analyzed and a base medium, such as ambient air. The second beam of light, on the other hand, passes through a reference cell 56 that includes the base medium, such as via a first reflector 58. As will be appreciated, the sample and base medium can have any of a number of different forms through which the first and second beams of light 50, 52 are at least partially transmissive. For example, the sample and base medium can comprise a solid, liquid, gas, plasma or aerosol. More particularly, in various advantageous embodiments, the base medium of ambient air is in aerosol form, while a sample of a chemical agent is in gas form and a sample of a biological agent is in aerosol form.

As the first beam of light 50 passes through the sample cell 52, the sample and base medium in the sample cell absorb at least a portion of the first beam, or more particularly at least a portion of the electric field of the first beam. The remaining, unabsorbed portion of the first beam of light 50' (i.e., sample signal) then exits the sample cell with a sample electric field $E_S$. Similarly, as the second beam of light 52 passes through the reference cell 54, the base medium in the reference cell absorb at least a portion of the second beam, or more particularly at least a portion of the electric field of the second beam. The remaining, unabsorbed portion of the second beam of light 52' (i.e., reference signal) then exits the reference cell with a reference electric field $E_R$. In both paths, the polarization of the sample and reference signals typically remains unchanged from the first and second beams that passed through the respective cells. Continuing the above example, then, the sample signal can have a 0° polarization, while reference signal can have a 90° polarization.

From the sample and reference cells 54, 56 the sample and reference signals 50', 52' are polarimetrically processed to generate sum and difference electric fields, as shown in block 86 of FIG. 7. More particularly, the sample and reference signals pass to a second polarizing beamsplitter 60. As shown, the sample signal passes to the second polarizing beamsplitter via a second reflector 62. The second polarizing beamsplitter, in turn, combines the sample and reference signals into a recombined signal 46' with an electric field $E_{OUT}$. In this regard, in one typical embodiment including both the first reflector 58 and the second reflector, the opticalpath lengths from the first polarizing beamsplitter 48 to the second polarizing beamsplitter are set equal to one another such that the second polarizing beamsplitter combines the sample and reference signals in phase. But as the electric fields of the sample and reference signals have a 90° polarization offset, the electric field of the recombined signal $E_{OUT}$ includes a first electric-field component at a first polarization and a second electric-field component at a second polarization. The first component and first polarization can then correspond to the electric field and polarization of the sample signal, while the second component and second polarization correspond to the electric field and polarization of the reference signal. Thus, for example, the recombined signal can include a sample electric-field component $E_S$ at a 0° polarization and a reference electric-field component $E_R$ at a 90° polarization.

Following the second polarizing beamsplitter 60, the recombined signal 46' passes to an analyzer 64 for dividing the recombined signal into two parts, a sum signal 66 and a difference signal 68. The analyzer can divide the recombined signal into a sum signal of light having a 45° polarization, and a difference signal of light having a 135° polarization. As indicated above, the sum signal has an electric field $E_y$ proportional to the sum of the electric fields of the sample and reference electric-field components (i.e., $E_y=(1/\sqrt{2})(E_S+E_R)$). In contrast, the difference signal has an electric field $E_x$ proportional to the difference of the electric fields of the sample and reference electric-field components (i.e., $E_x=(1/\sqrt{2})(E_S-E_R)$). Thus, in accordance with embodiments of the present invention, the analyzer generates an electric field sum $E_y$ and an electric field difference $E_x$ of the electric fields of the sample and reference signals 50', 52' from the sample and reference cells 54, 56. As indicated above and explained below, by generating the electric field difference, the system

40 of embodiments of the present invention is capable of detecting a measure of the absorption, and accordingly an absorption signature, of the sample in the sample cell with a reduced noise floor and thus increased sensitivity.

Following the analyzer 64, the sum signal 66 propagates to a first focusing lens 70a (e.g., lens 20a), from which the focused sum signal is picked up or otherwise received by a first receiver 72a (e.g., receiver 22a). Similarly, the difference signal 68 propagates to a second focusing lens 70b (e.g., lens 20b), from which the focused difference signal is picked up or otherwise received by a second receiver 72b (e.g., receiver 22b). The first and second receivers obtain measurements representative of the electric field sum $E_y$ and electric field difference $E_x$ of the sum and difference signals, respectively, as shown in block 88 of FIG. 7. As indicated above, the first and second receivers of one embodiment comprise a power detector and a photomixer receiver (heterodyne receiver), respectively. In this regard, by removing the large common mode electric field component from the electric field difference $E_x$, the photomixer receiver can operate with the largest theoretical gain to thereby provide superior noise performance, particularly when voltage noise of a post receiver amplifier operates as the dominant source of noise.

As indicated above, in the photomixer receiver 72b, the difference signal 68 at the transmitted frequency (e.g., $\omega_1 - \omega_2$) is combined with a local oscillator beam of light at a frequency $\omega_{LO}$, and thereafter focused on the photomixer. The photomixer receiver, in turn, operates in a manner similar to the photomixer transmitter to generate a current or voltage signal at an intermediate difference frequency (e.g., $\omega_1 - \omega_2 - \omega_{LO}$), where the generated signal varies as a result of radiation changes produced by the difference beam. By detecting changes in the generated signal, the photomixer receiver obtains a measure of the radiation, or electric field difference $E_x$.

Following the first receiver 72a, the measured sum power $(\Sigma E)^2$ can, but need not, be passed to a first amplifier 74a (e.g., amplifier 24a) having a first scaling constant $K_1$. Similarly, the measured electric field difference can, but need not, be passed from the second receiver 72b to a second amplifier 74b (e.g., amplifier 24b) having a second scaling constant $K_2$. Thereafter, the amplified, measured electric field sum and difference are received by a data acquisition processor 76 (e.g., processor 26). Like processor 26, the data acquisition processor can calculate the power ratio of the unabsorbed sample and reference signals 50', 52' based upon the measured sum power and electric field difference, as shown in block 90 of FIG. 7. Following the first and second amplifiers, then, the data acquisition processor receives the output of the first receiver as $V_D = K_1 \times \Sigma E^2$, and receives the output of the second receiver as $V_o = K_2 \times \Delta E$, as shown in FIG. 5. Following receipt of the amplified outputs, then, the data acquisition processor can calculate transmission of the sample in the sample channel based upon equation (7). More particularly, neglecting the second order terms of equation (7), the data acquisition processor can calculate the transmission T of the sample as follows:

$$T = \frac{P_S}{P_R} = 4 \times \left[\frac{\Delta E}{\Sigma E}\right] + 1 \tag{8}$$

Consider that the amplified outputs $V_D$ and $V_o$ can be rearranged into expressions for the electric-fields of the sum and difference signals, as follows:

$$\Delta E = \frac{V_o}{K_2}, \Sigma E = \sqrt{\frac{V_D}{K_1}} \tag{9}$$

Substituting the expressions (9) into equation (8), the transmission T of the sample can be expressed in terms of the amplified outputs $V_D$ and $V_o$ in accordance with the following equation (10):

$$T = 4\frac{\sqrt{K_1}}{K_2} \times \frac{V_O}{\sqrt{V_D}} + 1 = K_3 \times \frac{V_o}{\sqrt{V_D}} + 1 \tag{10}$$

where $K_3 = 4\frac{\sqrt{K_1}}{K_2}$.

In operation as a spectrometer, the system 40 scans through a number of transmission frequencies in a range of frequencies, such as by pumping the photomixer of the transmitter 42 with a laser source at a fixed frequency $\omega_2$, and a laser source at a tunable frequency $\omega_1$ that is scanned through a number of frequencies, as shown in blocks 92 and 94 of FIG. 7. For each transmission frequency in the range of frequency, and thus each beam of light 46 having a different transmission frequency, the data acquisition processor calculates the transmission T of the sample in the sample channel. The resulting collection of transmissions T and associated transmission frequencies define a measured absorption signature for the sample in the sample cell 54, normalized for the base medium in the sample cell and reference cell 56, as shown in block 96 of FIG. 7.

Embodiments of the present invention therefore provide an improved system and method of detecting the power of electromagnetic signals, as such may be applied in the context of spectroscopy. The dual, sample and reference channel system establishes a difference signal that, in the second (e.g., photomixer) receiver lowers the detector noise floor inversely proportional to the square root of the common mode power rejected. In this regard, consider for example, that rejecting a 1 milli-Watt common mode power to a residual level of 10 micro-Watts improves the noise equivalent transmission by a factor of 10.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system comprising:
   a receiver assembly for receiving a signal having a sample component with a sample electric field and a sample polarization, and having a reference component with a reference electric field and a reference polarization, the reference polarization being offset from the sample polarization, the receiver assembly comprising:
   an analyzer for polarimetrically processing the signal, wherein the analyzer is capable of differencing the signal to generate a difference electric field proportional to the difference of the sample and reference electric fields, the polarimetric differencing reducing a magnitude of a common-mode amplitude of the sample and reference electric fields, wherein the analyzer is further capable of summing the signal to generate a sum electric field proportional to the sum of the sample and reference electric fields; and an electric-field detector for measuring the difference electric field, the reduction in common-mode amplitude decreasing a noise equivalent power of the electric-field detector wherein the receiver assembly further comprises:

a power detector for measuring a sum power based upon the sum electric field; and a processor programmed to calculate a power ratio based upon the measured difference electric field and the measured sum power.

2. A system according to claim 1 further comprising:
a beamsplitter for generating first and second beams from a source beam;
a sample cell for receiving the first beam and outputting a sample signal with a sample electric field, the sample cell including a sample medium and a base medium;
a reference cell for receiving the second beam and outputting a reference signal with a reference electric field, the reference cell including the base medium, wherein the sample and reference signals have a polarization offset; and
a polarizing beamsplitter for combining the sample signal and the reference signal into the signal having the sample and reference components.

3. A system according to claim 2, wherein the processor is capable of calculating a power ratio of the sample signal and the reference signal based upon the measured difference electric field and the measured sum power, the power ratio being representative of a transmission of the sample.

4. A system according to claim 2, wherein the source beam has a transmission frequency, and wherein the system further comprises:

a transmitter for scanning the source beam through a plurality of transmission frequencies in a range of frequencies, wherein the beamsplitter, sample cell, reference cell, polarizing beamsplitter, analyzer, electric-field detector, power detector, and processor are capable of generating first and second beams, outputting a sample signal, outputting a reference signal, combining the sample and reference signals, measuring the difference electric field, measuring the sum power, and calculating a power ratio for each transmission frequency to obtain a power ratio for each transmission frequency, the power ratio at each transmission frequency being representative of a transmission of the sample, and wherein the processor is capable of defining a measured absorption signature for the sample medium based upon the transmissions and associated transmission frequencies.

5. A system according to claim 1, wherein the electric-field detector of the receiver assembly comprises a heterodyne receiver.

6. A method comprising:
receiving a signal having a sample component with a sample electric field and a sample polarization, and having a reference component with a reference electric field and a reference polarization, the reference polarization being offset from the sample polarization;
polarimetrically processing the signal, wherein the polarimetrically processing step includes differencing the signal to generate a difference electric field proportional to the difference of the sample and reference electric fields, and wherein the polarimetric differencing reduces a magnitude of a common-mode amplitude of the sample and reference electric fields, wherein the polarimetrically processing step further includes summing the signal to generate a sum electric field proportional to the sum of the sample and reference electric fields; and
measuring the difference electric field with an electric-field detector, the reduction in common-mode amplitude decreasing a noise equivalent power of the electric-field detector, wherein the method further comprises:
measuring a sum power with a power detector based upon the sum electric field; and
calculating a power ratio based upon the measured difference electric field and the measured sum power.

7. A method according to claim 6, further comprising:
generating first and second beams from a source beam;
propagating the first beam through a sample cell to thereby establish a sample signal with a sample electric field, the sample cell including a sample medium and a base medium;
propagating the second beam through a reference cell to thereby establish a reference signal with a reference electric field, the reference cell including the base medium, wherein the sample and reference signals have a polarization offset; and
combining the sample signal and the reference signal into the signal having the sample and reference components.

8. A method according to claim 6, wherein measuring the difference electric field comprises measuring the difference electric field with an electric-field detector comprising a heterodyne receiver.

* * * * *